United States Patent
Ehrman et al.

(10) Patent No.: US 12,144,882 B2
(45) Date of Patent: *Nov. 19, 2024

(54) METHOD OF IMPROVING THE APPEARANCE OF SKIN

(71) Applicant: The Procter & Gamble Company, Cincinnati, OH (US)

(72) Inventors: Matthew Clair Ehrman, Singapore (SG); Tomohiro Hakozaki, Cincinnati, OH (US); John Erich Oblong, Loveland, OH (US); Dissanayake Mudiyanselage Mahathma Bandara Dissanayake, Mason, OH (US); Wan Ting Chung, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/070,570

(22) Filed: Nov. 29, 2022

(65) Prior Publication Data

US 2023/0165778 A1 Jun. 1, 2023

Related U.S. Application Data

(60) Provisional application No. 63/283,733, filed on Nov. 29, 2021.

(51) Int. Cl.
| | |
|---|---|
| *A61K 8/67* | (2006.01) |
| *A61K 8/23* | (2006.01) |
| *A61K 8/34* | (2006.01) |
| *A61K 8/365* | (2006.01) |
| *A61K 8/368* | (2006.01) |
| *A61K 8/49* | (2006.01) |
| *A61Q 19/08* | (2006.01) |

(52) U.S. Cl.
CPC ............... *A61K 8/675* (2013.01); *A61K 8/23* (2013.01); *A61K 8/345* (2013.01); *A61K 8/365* (2013.01); *A61K 8/368* (2013.01); *A61K 8/4926* (2013.01); *A61Q 19/08* (2013.01); *A61K 2800/30* (2013.01); *A61K 2800/522* (2013.01); *A61K 2800/805* (2013.01)

(58) Field of Classification Search
CPC .......... A61K 8/675; A61K 8/23; A61K 8/345; A61K 8/365; A61K 8/368; A61K 8/4926; A61K 2800/30; A61K 2800/522; A61K 2800/805; A61K 8/36; A61Q 19/08
USPC ........................................................ 424/401
See application file for complete search history.

(56) References Cited

U.S. PATENT DOCUMENTS

| | | | |
|---|---|---|---|
| 6,632,444 B1 | 10/2003 | Zhou et al. | |
| 7,179,841 B2 | 2/2007 | Zielinski et al. | |
| 2005/0100517 A1 | 5/2005 | Sanzgiri et al. | |
| 2010/0189669 A1 | 7/2010 | Hakozaki | |
| 2014/0107046 A1 | 4/2014 | Pan et al. | |
| 2014/0161849 A1 | 6/2014 | Bickford | |
| 2014/0309294 A1 | 10/2014 | Erfurt et al. | |
| 2016/0101029 A1 | 4/2016 | Serrano Sanmiguel et al. | |
| 2016/0151270 A1 | 6/2016 | Brooks et al. | |
| 2018/0116936 A1 | 5/2018 | Pan et al. | |
| 2021/0346275 A1* | 11/2021 | Carle | A61Q 19/02 |
| 2023/0021127 A1 | 1/2023 | Maruyama | |
| 2023/0046148 A1 | 2/2023 | Stebbins et al. | |
| 2023/0165767 A1 | 6/2023 | Ehrman et al. | |

FOREIGN PATENT DOCUMENTS

| | | |
|---|---|---|
| CN | 106309156 A | 1/2017 |
| CN | 110638692 A | 1/2020 |
| CN | 112022766 A | 12/2020 |
| EP | 2906037 B1 | 8/2018 |
| WO | 0107004 A1 | 2/2001 |
| WO | 2005044214 A1 | 5/2005 |
| WO | 2008052674 A1 | 5/2008 |
| WO | 2011042073 A2 | 4/2011 |
| WO | 2013016257 A1 | 1/2013 |
| WO | 2019108450 A1 | 6/2019 |
| WO | 2020010036 A1 | 1/2020 |
| WO | 2020122088 A1 | 6/2020 |
| WO | 2021125070 A1 | 6/2021 |
| WO | 2021232040 A1 | 11/2021 |

OTHER PUBLICATIONS

16167M PCT Search Report and Written Opinion for PCT/US2022/080524 dated Apr. 4, 2023, 14 pages.
Database GNPD [Online] Mintel; anonymous: "Acne Eliminating Gel", Jul. 31, 2020, 6 pages, XP093033428, Database accession No. 7945189.
Database GNPD [Online] Mintel; anonymous: "Advanced Brighten Treatment Serum", Aug. 17, 2020, 6 pages, XP093033429, Database accession No. 7974155.
Database GNPD [Online] Mintel; anonymous: "Haute C Bright Serum Concentrate", Jul. 6, 2020, 7 pages, XP093033427, Database accession No. 7935589.
Nair Nirmala et al, "26415 Regulation of postinflammatory hyperpigmentation by niacinamide through potential modulation of the protease inhibitor, SERPINB3", Journal of the American Academy of Dermatology, Mosby, Inc, US, vol. 85, No. 3, Aug. 7, 2021, 1 page, XP086725903, ISSN: 0190-9622.
All Office Actions; U.S. Appl. No. 18/070,575, filed on Nov. 29, 2022.
All Office Actions; U.S. Appl. No. 18/070,863, filed on Nov. 29, 2022.
Unpublished U.S. Appl. No. 18/070,863, filed Nov. 29, 2022, to Matthew Clair Ehrman et al.

(Continued)

*Primary Examiner* — Frederick F Krass
*Assistant Examiner* — Lucy M Tien
(74) *Attorney, Agent, or Firm* — Alexandra S. Anoff

(57) ABSTRACT

Disclosed is a method of improving the appearance of skin with a low-pH skin care composition that contains hydroxycinnamic acid (HCA) and a vitamin B3 compound in a synergistic combination.

19 Claims, 2 Drawing Sheets

(56) References Cited

OTHER PUBLICATIONS

Unpublished U.S. Appl. No. 18/070,575, filed Nov. 29, 2022, to Matthew Clair Ehrman et al.
All Office Actions; U.S. Appl. No. 18/070,572, filed on Nov. 29, 2022.
Banish (2021, Ferulic Acid and What it does for your skin, URL Link-banish.com/blogs/ article/how-ferulic-acid-benefits-skin (Year: 2021), 3 pgs.
Capryloyl Salicylic Acid: 78418-01-6. Chemical Book, URL Link-www.chemicalbook.com/ChemicalProductProperly_EN_CB2959760(Year: 2023), 3pgs.
All Office Actions; U.S. Appl. No. 18/733,216, filed on Jun. 4, 2024.
Darwish et al. "Effects of Hydrotropic Agents on the Solubility, Precipitation, and Protein Binding of Etoposide", Journal of Pharmaceutical Sciences, vol. 78, Issue 7, Jul. 1989, pp. 577-581.
Unpublished U.S. Appl. No. 18/733,216, filed Jun. 4, 2024, Matthew Clair Ehrman et al.

\* cited by examiner

METHOD OF IMPROVING THE APPEARANCE OF SKIN

FIELD

The present invention relates to a method of improving the appearance of skin with a low-pH skin care composition that contains stable hydroxycinnamic acid (HCA) and a vitamin B3 compound in a synergistic combination.

BACKGROUND

Skin is the first line of defense against environmental insults that would otherwise damage sensitive underlying tissue and organs. Additionally, skin plays a key role in a person's physical appearance. Not surprisingly, most people would like to have heathy, younger looking skin. Unfortunately for some people, the tell-tale signs of aging such as thinning skin, wrinkles, and age spots are an undesirable reminder of the disappearance of youth. The desire for healthy, younger looking skin has led to the development of numerous skin care products marketed to treat the various skin conditions associated with aging and unhealthy skin. These skin care products typically include one or more active ingredients for treating a skin condition of interest.

Hydroxycinnamic acids (HCAs) are well-known skin care actives exploited for their powerful antioxidant properties, for example, as described in WO 2018/081790. However, the use of hydroxycinnamic acids in skin care composition can be problematic. For example, HCAs are relatively insoluble in water, which can lead to the undesirable formation of HCA crystals in the product. Further, when HCA is used at neutral pH (e.g., pH 5.0-8.0), which is becoming more common for certain skin care compositions, the HCA may oxidize or degrade, causing undesirable color changes, odors and/or reduced efficacy of the product. In some instances, formulating the composition at a lower pH may help stabilize the HCA, but it also lowers HCA solubility. Because of their potential use as multi-functional skin actives, there is much interest in overcoming the formulation and stability problems of HCAs.

In order to increase the solubility of HCA, some formulators use additional solvents such as glycols, for example, as described in U.S. Pat. No. 9,072,919. However, this approach can have undesirable tradeoffs on the sensory profile of the composition. In particular, high levels of glycols may cause a skin care composition to feel undesirably oily because glycols generally do not dry or absorb into the skin quickly. Other attempts to address the solubility issues of hydroxycinnamic acid is to formulate the material into the oil phase of the composition (i.e., in the case of an emulsion) or to encapsulate the material. But these approaches can also be problematic. For example, adding a hydroxycinnamic acid to the oil phase can undesirably affect the sensory profile of the composition due to the introduction of oils and additional emulsifiers to the composition, and encapsulation can reduce the amount of hydroxycinnamic acid in the composition due to encapsulate loading limits. Thus, there remains a need to provide a method of providing improved benefit, especially, improved appearance of skin, by using an aqueous composition containing hydroxycinnamic acid.

SUMMARY

Disclosed herein is a method of improving the appearance of skin comprising identifying a target portion of skin where treatment is desired and applying a low-pH, aqueous skin care composition to the target portion of skin over the course of a treatment period. The composition contains a vitamin B3 compound, hydroxycinnamic acid (HCA), and water, and has a pH of less than 5.0.

BRIEF DESCRIPTION OF THE DRAWINGS

The HPLC reference spectrum for HCA and 4-VP are shown in FIGS. 1A and 1B, respectively.

DETAILED DESCRIPTION

Figure 1A:
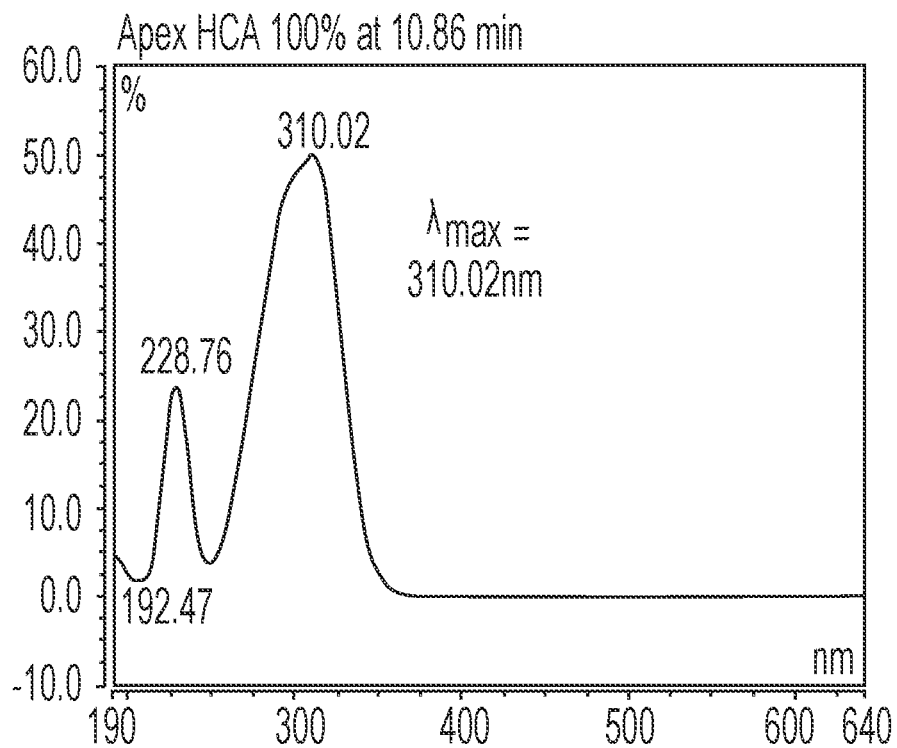
Figure 1B:
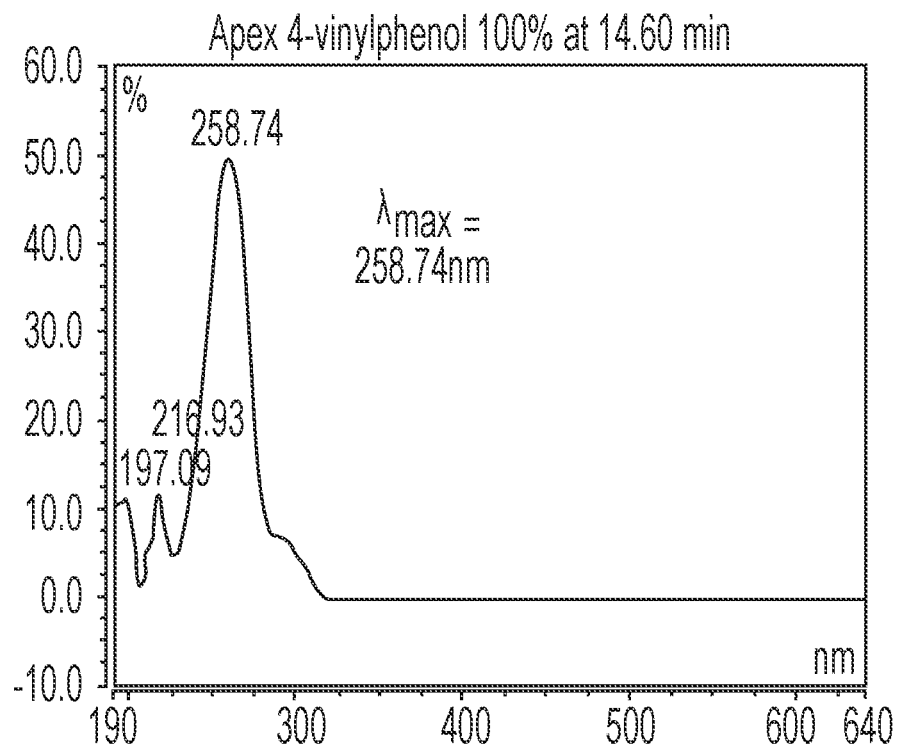

Hydroxycinnamic acids such as coumaric acid are known to be good antioxidants and are commonly used in skin care compositions as such. Surprisingly, it has now been discovered that a low-pH skin care composition containing HCA and niacinamide can synergistically improve the appearance of skin, especially sallow looking skin and skin texture and/or skin stability. Improved skin stability means to provide reduced day-to-day fluctuation of skin condition.

Additionally, in the preferred embodiments, it would be desirable to improve HCA solubility and/or stability in such compositions to deliver further improved synergistic skin appearance benefit.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all percentages are by weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

Definitions

"About" modifies a particular value by referring to a range equal to plus or minus twenty percent (+/−20%) or less (e.g., less than 15%, 10%, or even less than 5%) of the stated value.

"Apply" or "application," as used in reference to a composition, means to apply or spread the compositions of the present invention onto a human skin surface such as the epidermis.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, an effective amount of a vitamin B3 compound is an amount sufficient to improve the health and/or appearance of psoriatic skin during a treatment period. In some instances, an effective amount may be demonstrated using ex vivo and/or in vitro methods.

"Hydroxycinnamic acid" (HCA) refers to a class of aromatic acids or phenylpropanoids having a C6-C3 skeleton that are hydroxy derivatives of cinnamic acid. Some non-limiting examples of HCA are caffeic acid, cichoric acid, cinnamic acid, chlorogenic acid, diferulic acids, coumaric acids (p-, o-, and m-), ferulic acid, sinapinic acid, sinapic acid, and α-cyano-4-hydroxycinnamic acid.

"Improve the appearance of" means providing a measurable, desirable change or benefit in skin appearance, which may be quantified, for example, by a decrease in redness, inflammation, and/or plaque scales.

"Low-pH" means a pH of less than 5.0 (e.g., 1.5 to 4.9, 2.0 to 4.5, 2.5 to 4.0, or 3.5 to 4.0). A suitable method of determining the pH of a composition is described in more detail below.

"Neutral pH" means a pH of 5.0 to 8.0.

"Safe and effective amount" means an effective amount of an ingredient that is low enough to avoid serious side effects (within the scope of sound medical judgment).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Treatment period," as used herein, means the length of time and/or frequency that a material or composition is applied to a target skin surface.

Composition

The skin care compositions described herein are low-pH compositions intended for topical application to human skin to improve the appearance, health, and/or function of skin. The present compositions may be used for non-therapeutic (i.e., cosmetic) treatment of a variety of skin conditions. For example, the low-pH composition may be particularly suitable for improving the appearance of skin, especially improving sallow looking skin and skin texture, and/or skin stability.

The low-pH skin care compositions herein include a safe and effective amount of hydroxycinnamic acid (e.g., p-coumaric acid, a.k.a. 4-HCA or p-HCA), a vitamin B3 compound, and optionally a hydrotrope. The combination of HCA and vitamin B3 compound is specifically tailored to provide a synergistic improvement in the appearance of skin. In some aspects, the composition may include a silicone emulsifier, a polymer thickener that can tolerate low-pH environments, a low molecular weight silicone fluid, an acid-salt pH-buffering system (e.g., a lactic acid/sodium lactate buffering system), and/or other ingredients commonly found in topical skin care compositions. It is believed, without being limited by theory, that the combinations of ingredients disclosed herein provides a stable and efficacious skin care composition that has good feel properties and is gentle on skin.

Preferably, the low-pH compositions used in the method herein are formulated to provide improved HCA solubility in a low-pH environment. In an aqueous, low-pH skin care composition, HCA has a tendency to precipitate out of the composition and form crystals ("HCA crystals"), which can undesirably affect the look, feel, and/or efficacy of the composition. Conventional low-pH compositions often contain HCA crystals. However, in preferred embodiments of the present invention, the low-pH compositions herein contain a hydrotrope specifically selected to help solubilize the HCA and inhibit HCA crystallization, and thus are free of HCA crystals. A suitable method for determining whether a composition is free of HCA crystals and/or characterizing HCA crystals in a composition is described in more detail below.

Preferably the low-pH compositions herein are also formulated to provide improved HCA stability. HCAs are relatively good antioxidant materials, and thus tend to be oxidized and/or degrade over time, which can result in a skin care composition that exhibits an undesirable color change (e.g., yellowing), an undesirable odor, and/or reduced efficacy. Formulating at a lower pH can improve HCA stability by reducing the rate at which it is oxidized, but it may be desirable, in some aspects, to include an antioxidant in the low-pH composition to help further reduce oxidation and/or degradation of the HCA.

The low-pH skin care compositions herein can be made by mixing the ingredients with a dermatologically acceptable carrier using conventional methods known to those skilled in the art. The compositions may be provided in various product forms such as solutions, suspensions, lotions, creams, gels, toners, sticks, sprays, aerosols, ointments, cleansing liquid washes and solid bars, pastes, foams, mousses, shaving creams, wipes, strips, patches, electric-powered patches, hydrogels, film-forming products, facial and skin masks (with and without insoluble sheet), and the like. The composition form may follow from the particular dermatologically acceptable carrier chosen.

In some instances, the low-pH skin care composition herein may be in the form of an essence. An essence is a form of topical skin care composition in a relatively concentrated formula that typically has a lower viscosity than a conventional cream- or lotion-type skin care composition. An essence may be provided in the form of a low viscosity fluid that is marketed to specifically target a particular skin condition and/or be used in the first step of a skin care regimen. The skin care essence products herein can have a dynamic viscosity of 1 centipoise (cP) to 15,000 cP at 25° C. (e.g., 50 cP to 10,000 cP or 100 cP to 7,500 cP, 200 cp to 5,000 cp, or 300 cp to 2,500 cp). A method of determining the viscosity of the low-pH compositions is described in more detail in the Methods section below.

Hydroxycinnamic Acid

The low-pH skin care compositions herein include a safe and effective amount of HCA. The HCA may be present in the composition at 0.1% to 10% (e.g., 0.5% to 5% or 1% to 4%). Hydroxycinnamic acids are generally recognized as antioxidant phenolic compounds, which can be found in plants, mainly as a component of cell walls. See, H. K. Kuzaki et al., J. Agric. Food Chem., 50, 2161-68 (2002). In some aspects, it may be desirable to select coumaric acid for use in the low-pH composition, especially p-coumaric acid (a.k.a. 4-HCA). P-coumaric acid has the following structure:

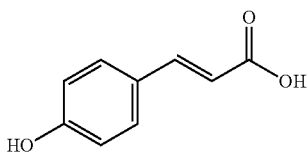 [SMILES: O=C(O)/C=C/c1ccc(O)cc1]

In other aspects, it may be desirable to use a mixture of two or more HCAs such as, for example, a mixture of coumaric acid and ferulic acid. In these aspects, the coumaric acid and ferulic acid may be present at a weight ratio of 2:1 to 1:2 (e.g., 1:1). A particularly suitable example of an HCA material suitable for use herein is LIPOBRITE available from Vantage Personal Care.

Vitamin $B_3$ Compound

The compositions include 0.1% to 10% (e.g., 0.5% to 5% or 1% to 4%) of a vitamin B3 compound. As used herein, "vitamin B3 compound" means a compound having the formula:

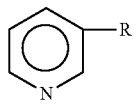

Where:
R is $CONH_2$ (i.e., niacinamide), COOH (i.e., nicotinic acid) or $CH_2OH$ (i.e., nicotinyl alcohol); derivatives thereof; and salts of any of the foregoing. Exemplary derivatives of vitamin B3 compounds include nicotinic acid esters, including non-vasodilating esters of nicotinic acid (e.g., tocopheryl nicotinate, myristyl nicotinate) nicotinamide riboside, nicotinyl amino acids, nicotinyl alcohol esters of carboxylic acids, nicotinic acid N-oxide, and niacinamide N-oxide. In some instances, vitamin B3 compounds such as niacinamide may have improved efficacy at lower pH, for example, as described in U.S. Publication No. 2020/0009123.

In some instances, it may be desirable for the ring nitrogen of the vitamin $B_3$ compound to be "uncomplexed" (e.g., chemically unbound and/or unhindered) in the composition and/or prior to application to a target skin surface. For example, the compositions herein may be free of or substantially free of (i.e., less than 3%, 2%, 1% or even less than 0.5%) a salt or complex of a vitamin B3 compound. Exemplary approaches to minimizing or preventing the formation of undesirable salts and/or complexes include omission of materials that form substantially irreversible or other undesirable complexes with the vitamin $B_3$ compound in the composition, pH adjustment, ionic strength adjustment, the use of surfactants, and practicing formulation processes wherein the vitamin $B_3$ compound and materials which complex therewith are in different phases.

Hydrotrope

HCA compounds generally exhibit especially poor solubility in a low-pH aqueous composition, such as the low-pH compositions described herein. For example, p-coumaric acid has a solubility of approximately 345 mg/mL in water at pH 7.0 and 20° C. and a solubility of 4 mg/mL in water at pH 3.0 and 20° C. Without being limited by theory, it is believed that the decreased solubility of an HCA at lower pH is due to reduced ability of the HCA to undergo the acid dissociation that forms the conjugate base species observed at higher pH levels. At pH 7, coumaric acid exists at approximately 99.6% in its conjugate base form; whereas at pH 3, the conjugate base form is only present at approximately 13.4%. As a result of its relatively poor solubility, HCA tends to form crystals in an aqueous, low-pH skin care composition. HCA crystals can impart an undesirable feel to the composition during use (e.g., a rough or grainy feel) and/or may decrease the efficacy of the HCA and/or other ingredients in the composition. This can create an undesirable consumer perception of poor product quality.

The compositions herein may include 0.1% to 10% (e.g., 0.5% to 5% or 1% to 3%) of a hydrotrope to enhance the water solubility of HCA. In some aspects, the hydrotrope may be a phenolic acid (e.g., salicylic acid) or a salt thereof (e.g., sodium salicylate). When the hydrotrope contains the conjugate base of a phenolic acid, the hydrotrope should have a pKA less than the formula pH and a sufficient intrinsic water solubility at the formula pH to be fully soluble. Having an acidic pKa that is less than the pH of the composition can be especially important for low-pH composition due to the reduced solubility of HCA at low pH. For example, sodium salicylate, which has a pKa of 2.8, would be a suitable hydrotrope for use in a composition with a pH of 3.8 because the associated carboxylic acid primarily exists in the conjugate base form. In contrast, sodium cinnamate, which have an acidic pKa of 4.32, respectively, would not be effective hydrotropes in this example. Additionally, the hydrotrope should be selected to help improve the sensory appeal of the composition by reducing the need for other solubilizing agents, such as glycols. Some non-limiting examples of hydrotropes that may be suitable for use herein are salicylic acid, 2, 4 dihydroxybenzoic acid, 2, 3 dihydroxybenzoic acid, 3-methoxy salicylic acid, salts of these, or a combination thereof. Other non-limiting examples of hydrotropes that may be suitable for use herein are disclosed in PCT Publication WO 2018/081790.

Anti-Oxidant

The low-pH composition herein may include an antioxidant to combat HCA oxidation and/or degradation. The antioxidant, when included, may be present at 0.001% to 3% (e.g., 0.01% to 2%, 0.05% to 1%, or 0.1% to 0.5%). Some non-limiting examples of antioxidants that may be suitable for use herein are sodium sulfite, sodium bisulfite sodium metabisulfite, and butylated hydroxytoluene.

Low-pH Acid Buffering System

When providing a low-pH composition for topical application to skin, it can be important to include a buffering system to help maintain the pH of the composition for a period of time after it is applied to the skin (e.g., up to 5 minutes or more). On average, human skin pH typically ranges from about 5.0 to 6.0. To maintain this pH, human skin has evolved a natural buffering system that resists changes to pH. Thus, when a low-pH composition is applied to the skin, the skin's natural buffering system will try to adjust the pH of the composition to match the natural pH of the skin. Without the addition of the buffering agent, the low-pH composition may not be able to provide the desired skin care benefit. Accordingly, the compositions herein may include a low-pH acid buffering system.

The buffering agent may be selected according to the acid(s) that is used to lower the pH of the low-pH compositions herein. For example, lactic acid and gluconic acid may be used to lower the pH of the composition because they are generally considered to be gentler on skin (i.e., lower risk of irritation) compared to other alpha hydroxy acids. In this example, sodium lactate or sodium gluconate would then be selected to provide the acid/salt pH buffer system. The buffering agent may be present in the low-pH composition at 0.25% to 4% (e.g., 0.5% to 3%, 0.75% to 2% or 1% to 1.75%). A non-limiting example of a suitable low-pH buffer system for use herein is disclosed in copending U.S. Ser. No. 16/891,491. Of course, it is to be appreciated that the present composition may optionally include other pH buffers known for use in skin care compositions.

Thickeners

The composition includes a polymer thickener that can tolerate a low-pH, electrolytic environment. That is, the thickener will not lose its ability to thicken or stabilize the composition at low-pH in the presence of an acid-salt buffering system. Some conventional neutralized thickeners are known to degrade and/or lose the ability to suitably thicken a composition at lower pH and/or in the presence of an acid-salt buffer (e.g., sodium lactate). For example, some neutralized thickeners degrade in a low-pH environment. On the other hand, fatty alcohol thickeners such as cetyl alcohols and stearyl alcohols are generally stable at low-pH, but tend to impart an undesirable cloudiness or opacity to the composition when it is in the form of an essence, serum, or the like. It has also been found that certain anionic polymeric thickeners can provide suitable tolerance to low-pH environments but cannot tolerate buffer systems due to combination of acid and salt. Thus, in some instances, the low-pH composition described herein may be free or substantially free of neutralized thickeners, fatty alcohol thickeners, and anionic thickeners. The thickener may be present at 0.0001% to 25% (e.g., 0.001% to 20%, 0.01% to 10%, 0.5% to 7%, or 1% or 5%) by weight of the composition.

Other nonlimiting examples of thickeners or water structuring agents that may be used alone or in combination herein include natural or synthetic gums, polysaccharides, carboxylic acid polymers, polyacrylamide polymers, sulfonated polymers, and copolymers of these. Further examples include modified gums, celluloses, and superabsorbent polymers. The term "superabsorbent polymer" is understood to mean a polymer which is capable, in its dry state, of spontaneously absorbing at least 20 times its own weight of aqueous fluid, in particular of water and especially of distilled water. Suitable polysaccharides include alkyl hydroxyalkyl cellulose ethers, such as hydroxypropylmethylcellulose stearoxy ether. This material is sold under the tradename of SANGELOSE 60L and 90L from Daido Chemical Corp. Another suitable polysaccharide includes hydrophobically modified starch, such as Potato modified starch. This material is sold under the tradename of STRUCTURE SOLANACE by Nouryon. Another polymer includes crosslinked polymers, the monomers of which are at least partially composed of acryloyldimethyltaurate monomers, such as, for example sodium polyacryloyldimethyl taurate, sold under the tradename of ARISTOFLEX SILK, from Clariant.

It has now been found that certain anionic polymeric thickeners can provide suitable tolerance to low-pH environments and the desired feel and opacity properties to the composition. Thus, a particularly suitable example of an anionic thickener is polyacrylate crosspolymer-6, which is commercially available as SEPIMAX ZEN from Seppic, France.

Low Molecular Weight Silicone Fluid.

In some instances, an anionic polymeric thickener may impart an undesirable tacky feel when the low-pH composition is applied to a target portion of skin. It has been found that the addition of a low molecular weight silicone fluid can reduce or prevent this tacky feel. The molecular weight of a silicone fluid depends on the length of its silicone polymer chain(s), which is also directly proportional to the viscosity of the silicone fluid. Thus, the low molecular weight silicone fluids suitable for use in the present low-pH composition have a kinematic viscosity of 100 cSt or less at 25° C. (e.g., 1 cSt to 90 cSt, 5 cSt to 50 cSt, or even 10 cSt to 30 cSt). Kinematic viscosity is a common method of classifying silicone fluids and can be obtained from the supplier of the material. A particularly suitable example of a low molecular weight silicone fluid is 5 cSt dimethicone fluid. As used herein, "dimethicone" means a polydimethylsiloxane compound having the formula:

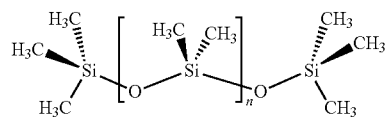

Dermatologically Acceptable Carrier

The low-pH compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight of the composition.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the vitamin B3 compound can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Emulsifier

When the low-pH composition herein is in the form of an emulsion (e.g., oil-in-water emulsion), it may be desirable to include an emulsifier to stabilize the emulsion (i.e., prevent the emulsion from phase separating). The emulsifier may be present in the composition at 0.01% to 10% (e.g., 0.05% to 5% or 0.1% to 2%). The emulsifiers may be nonionic, anionic or cationic. In some instances, the emulsifier may be a silicone emulsifier. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-324 (1986).

Some other non-limiting examples of emulsifiers that may be suitable for use herein include ethers of polyglycols and of fatty alcohols, esters of polyglycols and of fatty acids, ethers of polyglycols and of fatty alcohols which are glycosylated, esters of polyglycols and of fatty acids which are glycosylated, ethers of C12-30 alcohols and of glycerol or of polyglycerol, esters of C12-30 fatty acids and of glycerol or of polyglycerol, ethers of oxyalkylene-modified C12-30 alcohols and of glycerol or polyglycerol, ethers of C1-230 fatty alcohols comprising and of sucrose or of glucose, esters of sucrose and of C1230 fatty acids, esters of pentaerythritol and of C12-30 fatty acids, esters of sorbitol and/or of sorbitan and of C12 30 fatty acids, ethers of sorbitol and/or of sorbitan and of alkoxylated sorbitan, ethers of polyglycols and of cholesterol, esters of C12-30 fatty acids and of alkoxylated ethers of sorbitol and/or sorbitan, and combinations thereof. A particularly useful class of emulsifiers is polyethylene glycol ethers of lauryl alcohol such as laureth-1 through laureth-50 (e.g., laureth-4). Still other examples of emulsifiers include ethers of glycerol, polyglycerol, sucrose, glucose, or sorbitol; esters of glycerol, polyglycerol, sucrose, glucose, or sorbitol; and mixtures thereof. Other particularly useful classes of emulsifiers are the alkyl esters of sorbitol and sorbitol anhydrides such as polysorbate 20, polysorbate 21, and polysorbate 40.

In some aspects, it may be desirable to include a linear or branched silicone emulsifier in the low-pH composition. Particularly useful silicone emulsifiers include polyether modified silicones such as KF-6011, KF-6012, KF-6013, KF-6015, KF-6015, KF-6017, KF-6043, KF-6028, and KF-6038 and polyglycerolated linear or branched siloxane emulsifiers such as KF-6100, KF-6104, and KF-6105; all from Shin-Etsu. A particular suitable emulsifier for use herein is PEG-11 methyl ether dimethicone, which is available from Shin-Etsu as KF-6011. Surprisingly, it was discovered that the PEG-11 methyl ether dimethicone emulsifier further reduced the tacky feel of the anionic polymer thickener, thereby improving the overall feel of the low-pH composition. The emulsifier may be present at an amount of 0.1% to 10% (e.g., 1% to 5%, or 2%-4%).

Co-Solvent

In some aspects, the compositions herein may include a short chain dihydric alcohol (e.g., glycol) co-solvent to help solubilize the HCA. However, when glycol is selected as the co-solvent, it can be important to limit the amount of glycol to less than 25% (e.g., less than 20%, 17%, 15%, or even less than 10%) to reduce the risk of imparting undesirable feel characteristics to the composition having (e.g., sticky feeling or greasy feeling). Some non-limiting examples of glycols that may be suitable for use herein are propylene glycol, dipropylene glycol, butylene glycol, pentylene glycol, hexylene glycol, ethoxydiglycol, and C2-C6 polyethene glycols (e.g., PEG-3, PEG-4, PEG-4 methyl ether), and combinations thereof Other Optional Ingredients The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

When including optional ingredients in the compositions herein, it may be desirable to select ingredients that do not form complexes or otherwise undesirably interact with other ingredients in the composition at low-pH, especially pH sensitive ingredients like niacinamide, salicylates and peptides. In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Method of Use

The low-pH compositions herein are formulated for topical application to skin. The method of using the present low-pH composition involves identifying a target portion of skin on a person in need of treatment or where treatment is desired (e.g., portions of skin exhibiting sallowness, hyperpigmented spots, enlarged pores, or uneven skin color or texture) and applying an effective amount of the low-pH composition to the target portion of skin over the course of a treatment period. The effective amount of composition may vary based on the skin benefit desired by the user and/or the size of the treatment area. In some instances, the effective amount may range from 0.1 g to 5 g (e.g., 0.2 g to 4 g, 0.3 g to 2 g, or even 0.5 g to 1 g). The target portion of skin may be on a facial skin surface such as the forehead, perioral, chin, periorbital, nose, and/or cheek) or another part of the body (e.g., hands, arms, legs, back, chest). In some instances, a target portion of skin may be selected that does not currently exhibit signs of skin aging, but is an area of skin that commonly exhibits such features with age. In these instances, the low-pH composition may be used to help prevent the occurrence of such undesirable skin features.

The composition may be applied locally to the target portion of skin in need of treatment and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions may improve the appearance and/or function of skin, for example, by improving skin texture. Improvements in skin texture can be provided, for example, by decreasing pore size, reducing skin roughness, reducing the presence and/or size of wrinkles, combinations of these and the like.

The treatment period is ideally of sufficient time for the low-pH composition to improve the appearance and/or function of the target portion of skin. The treatment period typically lasts for at least 1 week (e.g., about 2 weeks, 4 weeks, 8 weeks, or even 12 weeks). In some instances, the treatment period may extend over multiple months (i.e., 3-12 months). In some instances, the composition is applied most days of the week (e.g., at least 4, 5 or 6 days a week), at least once a day or even twice a day during a treatment period of at least 2 weeks, 4 weeks, 8 weeks, or 12 weeks.

The step of applying the composition herein may be accomplished by localized application. In reference to application of the composition, the terms "localized", "local", or "locally" mean that the composition is delivered to the targeted area (e.g., a psoriatic plaque) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Methods

HPLC

This method provides a way to determine the weight percentage of HCA and 4-vinylphenol (4-VP), respectively, in raw materials or finished products using high performance liquid chromatography ("HPLC"). This method may also be used to identify HCA and/or 4VP, by matching their wavelength spectrum and retention time to their respective known standards. The following instruments and materials are used in this method:

Instruments:
  a gradient HPLC system that includes a gradient HPLC pump, liquid auto-sampler, UV detector (and diode array detector (DAD) for spectrum analysis), and a suitable computing integrator or computer data system (e.g., a Waters 2695 HPLC system from Waters Corporation or equivalent).
  a 5 um, 250 mm×4.6 mm ID HPLC column (e.g., a C18 column from Alltech Alltima).

Method:
Two mobile phases are used to create the gradient with a consistent flow rate of 1.0 mL/min. Mobile phase A consists of 0.5% acetic acid in purified water. Mobile phase B consists of 0.5% acetic acid in acetonitrile. The gradient is illustrated below in Table 1.

TABLE 1

| Analysis Time | Mobile Phase Composition (v/v) | |
|---|---|---|
| | % A | % B |
| 0.00 | 90 | 10 |
| 6.00 | 90 | 10 |
| 7.00 | 50 | 50 |

TABLE 1-continued

| | Mobile Phase Composition (v/v) | |
|---|---|---|
| Analysis Time | % A | % B |
| 12.00 | 50 | 50 |
| 13.00 | 30 | 70 |
| 16.00 | 30 | 70 |

Calculations:
1. Calculation of wt % of HCA in test samples $$HCA\ Wt\ \% = \frac{A \times M \times P \times 100}{B \times W}$$

A=Peak area ratio of HCA:Internal Standard in sample
B=Peak Area ratio of HCA:Internal Standard in Calibration Standard
M=Mass of HCA in mg, in Calibration Standard (~50 mg/50 mL×3 mL)
W=Sample weight in mg
P=Purity of HCA in decimal 2. Calculation of wt % of 4-VP in Finished Product Samples $$4VP\ Wt\ \% = \frac{a \times m \times p \times 100}{b \times w}$$

a=Peak area ratio of 4-VP: Internal Standard in sample
b=Peak area ratio of 4-VP: Internal Standard in Calibration Standard
m=Mass of 4-VP in mg, in Calibration Standard (~150 mg/100 mL×1 mL)
W=Sample weight in mg
p=Purity of 4-VP in decimal HCA Crystallization This method provides a way to determine HCA solubility in a composition by observing HCA crystals in situ. The method involves cycling the temperature of a test sample between freezing and thawing to imitate environmental conditions experienced by a skin care composition at an accelerated rate. This type of accelerated aging is commonly used in cosmetic product stability testing. HCA crystals can be detected using conventional means such as visual observation and microscopy.

A bulk sample of at least 10 g (e.g., 20 g-60 g) of the composition to be tested is placed in a suitable container that enables visual observation of the test sample (e.g., transparent plastic or glass jar). The test sample is subjected to 1 month of freeze/thaw temperature cycling to simulate environmental conditions that a skin care product may experience during shipping and storage. This is sometimes referred to as accelerated aging. The temperature cycling involves a 1-week freeze cycle at −7° C., followed by a 1-week thaw cycle at 25° C., and then repeating this freeze/cycle for a total temperature cycling time of 1 month.

Upon completion of the accelerated aging process (i.e., 1 month of temperature cycling), transparent test samples are visually inspected in-situ in the transparent container to determine if HCA crystallization/precipitation occurred. For opaque and translucent samples, the entire test sample is removed from the container and transferred to a suitable transparent substrate (e.g., plastic film or glass plate) and formed into a thin film of no more than 1 mm thickness. The sample is covered with a second transparent substrate to inhibit the loss of volatile ingredients during inspection. A light source (e.g., LED lamp or the like) is used to backlight the sample to aid in visual inspection. HCA crystals will generally appear as a precipitate in the composition visible to the naked eye when observed by someone with 20/20 vision from 45 cm away. Any precipitate identified during visual observation may be further evaluated using a microscope capable of providing fluorescent birefringence observation with cross-polarized light to identify anisotropic crystals. Any anisotropic crystal that has a longest dimension of greater than 0.1 mm is identified as an HCA crystal and the total number of HCA crystals is recorded. A test sample that contains no more than 1 HCA crystal is considered to be "free of HCA crystals" and is recorded as a "pass." A test sample that contains more than 1 HCA crystal, is recorded as a "fail."

While not required, fourier-transform infrared spectroscopy (FTIR) can be used to confirm that the HCA crystal or co-crystal contains the appropriate hydroxycinnamic acid structure. FTIR spectroscopy techniques are well-known in the art. See, U.S. Pat. No. 10,912,857, US2020/0000697, and Fourier Transform Infrared Spectroscopy in Colloid and Interface Science, D. R. Scheuing, Ed., American Chemical Society, 225, 1991.

Color

This method can be used to determine the change in color of a product, material, or substrate. A spectrophotometer (e.g., Spectrophotometer CM-3600A, Konica Minolta, Japan, or equivalent) is used to measure spectrometric data for CIE (International Commission on Illumination) specified illuminating and viewing conditions, and compute the associated tristimulus values, XYZ, based on CIE observer and a CIE illuminant standards. The ASTM standard for obtaining spectrometric data for Object-Color Evaluation is ASTM E1164-12(2017)e1 with the values and procedures for computing CIE tristimulus values from spectrometric data outlined in ASTM E308. The CIELAB color scale, also referred to as L*a*b*, are calculated from the tristimulus values as defined in ASTM E308. The L* denotes the sample's perceptual lightness. Whereas a* and b* relate to the unique colors of human vision, with a* being positive in the red direction and negative in the green direction, and b* positive in the yellow direction and negative in the blue direction.

The spectrophotometer is operated with a 2° observer and D65 illuminant to measure 1931 CIE defined tristimulus XYZ values with and associated CIELAB colors. Portion samples are evaluated using a 10 mm path length in a plastic cell (e.g., CM-A131, Konica Minolta, Japan or equivalent), reflectance measurement, a 25.4 mm aperture opening at the specimen surface, and specular component excluded conditions with a standard white background. Acceptable white backgrounds include the white portion of an opacity card or equivalent (e.g., opacity card Form 2A, Leneta Company, Inc, Mahwah, NJ). The instrument is calibrated with a zero standard, utilizing a zero-calibration box, or black trap, that is free from dust and debris (e.g., Konica Minolta zero calibration box CM-A155 or equivalent). The CIELAB values are reported by the associated instrument software (e.g., SpectroMagic NX) as defined in ASTM E308. For changes in product yellowness, the CIELAB color scale is utilized focused on the change in the b* value. The results are reported as a Δb*, where a positive Δb* indicates increased yellowness.

Rheology

This method provides a way to measure the dynamic viscosity of a composition or material using a BROOKFIELD brand viscometer (e.g., model DV2T or equivalent) and a suitable spindle (e.g., RV4 or equivalent) according to the manufacturer's instructions. It is to be appreciated that the skilled artisan will be able to select the appropriate spindle in accordance with the manufacture's recommendation. After calibrating the viscometer, the spindle is immersed into a sufficient quantity of test sample (e.g., enough to immerse the spindle up to the immersion mark on the spindle shaft). Set the spindle rotation speed to 5 rpm, and then start the viscometer. Allow time for the indicated viscosity reading to stabilize (approximately 10-30 seconds). After the reading stabilizes, take 5 readings at 10 second intervals. Calculate the viscosity as the average of the 5 readings.

Skin Stability Method

Skin appearance stability was measured using an eMR Pro which is a self-facial imaging system developed by P&G Company, Kobe, Japan (IP filing ref. number AA1280), and further described by Miyamoto, Kukizo, et al. "Daily fluctuation of facial pore area, roughness and redness among young Japanese women; Beneficial effects of Galactomyces ferment filtrate containing antioxidative skin care formula." Journal of clinical medicine 10.11 (2021): 2502. The method utilizes a commercial smartphone camera/LED lighting source (iPhone 7/8/SE) along with a plastic attachment over the facial cheek area. The attachment is equipped to control the intensity of the LED light illuminating the skin surface. Furthermore, a color chip is present for image standardization of each image. A small repositioning mirror and auto eye/face live-view recognition algorithm is incorporated into the eMR application program. Captured images (1080× 1920 pixels) are encrypted and subsequently analyzed after the region of interest is masked, alignment, and color standardization is complete. The device enables increase measurements by conducting the imaging at home by the panelists themselves. The plastic face attachment ensures constant distance between camera head and skin surface. Image analysis methods are conducted to measure skin features such as pores, spots, color such as L*,a*,b* and uneven appearance as described in the section below.

The method used to define unevenness appearance leverages entropy statistics is described in US patent (U.S. Pat. No. 11,348,366B2). The term entropy as used herein refers to a Shannon entropy (E) of a discrete random distribution (p(x)) and is defined by the following equation:

$$E(p) = -\sum_{x} p(x) \times \log p(x)]$$

wherein p(x) is the distribution of grey levels. E(p) represents the amount of information in a digital image or a color channel image in a color system after conversion of the digital image to the color channel image. "Entropy statistics" as used herein refers to a statistical method that uses entropy as a descriptive statistic for analyzing digital images or color channel images.

In a non-limiting example wherein the digital image is an RGB image, entropies (entropy values) for each R (red), G(green) and B(blue) channel can be calculated separately. The entropy value of an image can be calculated by calculating at each pixel position (i,j) the entropy value of the pixel-values within a 2-dimensional region centered at (i,j). The 2-dimensional region may be a part of a color channel image. Programming software packages such as Python may be used to calculate the entropy value. Color channels may be analyzed individually to isolate distinct tone and texture uneveness. When images are acquired in the red, green, blue, color channels, they may be converted to L*a*b* color coordinates for further descriptive analysis. When the red color channel is in the L*a*b* color system, a-entropy is an entropy value of the filtered red color channel. When the yellow color channel is in the L*a*b* color system, b-entropy is an entropy value of the filtered yellow color channel. When the blue color channel corresponds to a texture channel, c-entropy is an entropy value of the blue color channel.

The measure of variability to characterize skin stability from the time series data acquired used to characterize skin stability is the mean absolute difference for a given measured endpoint.

$$Y = \frac{1}{n}\sum_{i=0}^{n}|x_{i,j} - \overline{X}_J|$$

Y=mean absolute difference
n=number of observations
i=individual data point number
j=set of measurements (e.g. morning, evening, etc.)
x=individual measurement
$\overline{X}_j$=mean value of all data points (for the j set)

The individual measurements were taken at different consistent time points through the day. In the case of the described examples the measurement set was as follows: morning before face wash, morning after face wash, evening after face wash. The day-to-day fluctuations was then calculated by using mean absolute difference equation for a certain time point (e.g., evening after face wash). Programming software such as Python may be used to calculate the mean absolute difference.

Examples

Example 1: Formulations

Table 2 below provides examples of low-pH skin care compositions that correspond to various aspects of the invention. The compositions can be prepared using conventional methods of making skin care compositions. Such methods typically involve mixing of the ingredients in one or more steps to a relatively uniform state, with or without heating, cooling, application of vacuum, and the like. All exemplified amounts exclude minor materials such as diluents, preservatives, color solutions, feel modifying powders and elastomers, etc., that may be present in a commercial product unless otherwise specified. HCA may be added as a solid form and solubilized in-situ, dissolved as a premix, or supplied as a predispered raw material. A predispersed 15% solution of 4-HCA in PEG-4 (Lipobrite® from Vantage) is used for certain examples. For examples containing Lipobrite®, the 4-HCA and PEG-4 constituent levels are listed individually for clarity, with a superscript to denote the Lipobrite® raw material. The total Lipobrite® material added is the sum of the 4-HCA and PEG-4 constituents listed. All other materials are listed 'as is' from the suppliers and not broken down into the individual constituents.

Emulsions are prepared by first mixing the aqueous phase materials separately from the oil and/or silicone phase materials and then combining the two phases as appropriate to yield the desired continuous phase. In some aspects, the exemplary compositions can be made by blending the aqueous phase components with a suitable mixer (e.g., IKA RW20 or equivalent) until all materials are dissolved and homogeneous. When present, the optional polymer thickener may be hydrated by slowing adding the thickener directly into a water phase while stirring and continued mixing until homogeneous. The 4-HCA, hydrotrope, and optional glycol may be added together in a separate pre-mix container and mixed until fully dissolved and uniform. In some aspects, the hydrotrope may be pre-neutralized to form a suitable salt (e.g., sodium salicylate) to promote mixing/solubilization. The HCA premix can then be added to the main mix container and further mixed until homogeneous. The formula can be milled using a suitable mixer (e.g., IKA Ultra Turrax T-25 or equivalent) to reduce the emulsion particle size until a target viscosity is reached and uniform composition is achieved. The temperature may be adjusted as needed to control the speed of the process and/or achieve a homogenous final product.

TABLE 2

| Component | 2A | 2B | 2C | 2D | 2E | 2F | 2G |
|---|---|---|---|---|---|---|---|
| | | | % | | | | |
| Water | qs | qs | qs | qs | qs | qs | qs |
| Glycerin | 7.00 | 3.00 | 3.00 | 3.00 | 3.00 | 3.00 | 3.00 |
| Dimethicone 5 cSt | — | — | 2.00 | 2.00 | 2.00 | 2.00 | 2.00 |
| Niacinamide | 2.00 | 2.00 | 2.00 | 2.00 | 2.00 | 5.00 | 2.00 |
| Lactic acid | 1.80 | 1.80 | 1.80 | 1.80 | 1.80 | 1.80 | 1.80 |
| Sodium lactate | 1.30 | 1.30 | 1.30 | 1.30 | 1.30 | 1.30 | 1.30 |
| Polyacrylate crosspolymer-6 [1] | — | — | 1.25 | 1.25 | 1.25 | 1.25 | 1.25 |
| Sodium polyacryloyldimethyl taurate [2] | 1.25 | 1.25 | — | — | — | — | — |
| D-Panthenol | 0.50 | 0.50 | 0.50 | 0.50 | 0.50 | 0.50 | 0.50 |
| Disodium EDTA | 0.10 | 0.10 | 0.10 | 0.10 | 0.10 | 0.10 | 0.10 |
| PEG-11 methyl ether dimethicone [3] | — | — | 0.10 | 0.10 | 0.10 | 0.10 | 0.10 |
| Trehalose | — | — | 0.50 | 0.50 | 0.50 | 0.50 | 0.50 |
| Sodium benzoate | 0.05 | 0.05 | 0.05 | 0.05 | 0.05 | 0.05 | 0.05 |
| Sodium sulfite | — | 0.05 | 0.05 | 0.05 | 0.05 | 0.05 | 0.05 |
| 4-HCA [4] | 0.0001 | 1.00 | 0.50 | 0.25 | 0.10 | 1.00 | 0.30 |
| PEG-4 [4] | 0.00057 | 5.67 | 2.83 | 1.42 | 0.57 | 5.67 | 1.7 |
| Pentylene glycol | 0.10 | 3.00 | — | 3.00 | 3.00 | 3.00 | 3.00 |
| Propylene glycol | — | 5.00 | — | — | — | 5.00 | 5.00 |
| Dipropylene glycol | — | 4.00 | — | — | — | 4.00 | 4.00 |
| Ethoxydiglycol | — | 12.00 | 12.00 | 7.50 | 5.00 | 12.00 | 2.60 |
| Sodium Salicylate | — | 1.50 | 1.50 | 1.50 | 1.50 | 1.50 | 0.50 |
| Isohexadecane | 3.00 | 3.00 | — | — | — | — | — |
| Isopropyl Isostearate | 1.50 | 1.50 | — | — | — | — | — |
| Cetearyl glucoside and cetearyl | 0.50 | 0.50 | — | — | — | — | — |
| Behenyl Alcohol | 0.70 | 0.70 | — | — | — | — | — |
| Stearyl Alcohol | 1.20 | 1.20 | — | — | — | — | — |
| Cetyl Alcohol | 0.90 | 0.90 | — | — | — | — | — |
| PEG-100 Stearate | 0.10 | 0.10 | — | — | — | — | — |
| Stearic Acid | 0.10 | 0.10 | — | — | — | — | — |
| Dimethicone and Dimethiconol [5] | 1.00 | 1.00 | — | — | — | — | — |
| Palmitoyl pentapeptide-4 [6] | 0.50 | 0.50 | — | — | — | — | — |
| NaOH (pH adjuster) | * | * | * | * | * | * | * |
| HCl (pH adjuster) | * | * | * | * | * | * | * |
| pH | 4.0 | 4.0 | 4.0 | 4.0 | 3.0 | 5.0 | 3.8 |

| Component | 2H | 2I | 2J | 2K | 2L | 2M | 2N |
|---|---|---|---|---|---|---|---|
| | | | % | | | | |
| Water | qs | qs | qs | qs | qs | qs | qs |
| Glycerin | 3.00 | 3.00 | 3.00 | 7.00 | 3.00 | 3.00 | 3.00 |
| Dimethicone 5 cSt | 2.00 | 2.00 | — | — | 2.00 | 2.00 | 2.00 |
| Niacinamide | 2.00 | 2.00 | 2.00 | 0.25 | 0.50 | 0.50 | 2.00 |
| Lactic acid | 1.80 | 1.80 | 1.80 | 1.80 | 1.80 | 1.80 | 1.80 |
| Sodium lactate | 1.30 | 1.30 | 1.30 | 1.30 | 1.30 | 1.30 | 1.30 |
| Polyacrylate crosspolymer-6 [1] | 1.20 | 1.20 | 1.20 | 1.25 | 1.20 | 1.20 | 1.20 |
| Sodium polyacryloyldimethyl taurate [2] | — | — | — | — | — | — | — |
| Panthenol | 0.50 | 0.50 | 0.50 | 0.50 | 0.50 | 0.50 | 0.50 |
| Disodium EDTA | 0.10 | 0.10 | 0.10 | 0.10 | 0.10 | 0.10 | 0.10 |
| PEG-11 methyl ether dimethicone [3] | 0.10 | 0.10 | 0.10 | — | 0.10 | 0.10 | 0.10 |
| Trehalose | 0.10 | 0.10 | 0.10 | 0.10 | 0.10 | 0.10 | 0.10 |
| Sodium benzoate | 0.05 | 0.05 | 0.05 | 0.05 | 0.05 | 0.05 | 0.05 |
| Ferulic acid [7] | 0.25 | 0.25 | 0.25 | — | — | — | — |
| 4-HCA [4] | 0.25 | 0.25 | 0.25 | 0.10 | 0.5 | 0.5 | 0.5 |
| PEG-4 [4] | 1.42 | 1.42 | 1.42 | 0.57 | 2.83 | 2.83 | 2.83 |
| Pentylene glycol | 3 | — | — | — | — | — | — |
| Propylene glycol | — | — | — | — | — | — | — |
| Dipropylene glycol | — | — | — | — | — | — | — |
| Ethoxydiglycol | 15 | 15 | 15 | 5.00 | 15 | 20 | 15 |
| Sodium salicylate | — | 0.5 | 0.5 | 0.75 | 1.5 | 1.5 | 1.5 |
| Isohexadecane | — | — | 3.00 | 3.00 | — | — | — |
| Isopropyl isostearate | — | — | 1.50 | 1.50 | — | — | — |
| Cetearyl glucoside and cetearyl | — | — | 0.50 | 0.50 | — | — | — |
| Behenyl alcohol | — | — | 0.70 | 0.70 | — | — | — |

TABLE 2-continued

| | | | | | | | |
|---|---|---|---|---|---|---|---|
| Stearyl alcohol | — | — | 1.20 | 1.20 | — | — | — |
| Cetyl alcohol | — | — | 0.90 | 0.90 | — | — | — |
| PEG-100 stearate | — | — | 0.10 | 0.10 | — | — | — |
| Stearic acid | — | — | 0.10 | 0.10 | — | — | — |
| Dimethicone and dimethiconol [5] | — | — | 1.00 | 1.00 | 1.00 | — | — |
| Palmitoyl pentapeptide-4 [6] | — | — | 0.5 | 0.50 | — | — | — |
| NaOH (pH adjuster) | * | * | * | * | * | * | * |
| HCl (pH adjuster) | * | * | * | * | * | * | * |
| pH | 4.0 | 4.0 | 4.0 | 2.5 | 3.0 | 2.5 | 4.0 |

[1] SEPIMAX ZEN available from Seppic
[2] ARISTOFLEX SILK available from Clariant
[3] KF-6011 available from Shin-Etsu
[4] LIPOBRITE from Vantage (15% 4-HCA, 85% PEG-4)
[5] DC 1503 from Dow Corning
[6] PROMATRIXYL from Croda
[7] Ferulic Acid from Sigma Aldrich
* pH adjustment as necessary

Example 2: Synergistic Reduction in Δb* and Skin Texture

The example demonstrates the ability of the low-pH compositions herein to provide a synergistic improvement in the appearance of sallow-looking skin in a clinical study. Three independent clinical studies were conducted to study the beneficial skin effects provided by the present compositions. Each clinical test was a 9-week in vivo study using a randomized, vehicle controlled, round robin, split face design including a 1-week washout period and an 8-week test period. All results reported are the 8-week test period results. The minimum base size per study was forty subjects. The treatment regimen began with a 1-week washout period. Each morning and evening the subject was instructed to wash her face with standard cleanser (Olay Deep cleansing facial Cleanser, available from The Procter & Gamble Company), gently dry with a towel, and apply a standard moisturizer (with 3% glycerin) to both sides of face. At baseline, each subject received two coded test formulations for twice daily application to either the left or right side of the face. Each morning and evening the subject was to wash her face with standard cleanser, gently dry with a towel, and apply 0.5 g of the appropriate test formulation on each side of the face with the fingers using gentle pressure in a circular motion. Positive and negative (vehicle) controls were used in each study. The positive control was a neutral pH composition that contained 5% niacinamide and 1% undecylenoyl phenylalanine (SEPIWHITE from Seppic), which is a known skin brightening agent. Test leg A contained 0.9% coumaric acid (6% LIPOBRITE from Vantage), test leg B was a low-pH (3.8) composition containing 2% niacinamide, and leg C was an inventive low-pH composition containing 2% niacinamide and 1% coumaric acid (6.67% LIPOBRITE). The results of the testing are summarized in Tables 3 and 4.

Images of the facial treatment sites were captured at baseline and 8 weeks of treatment and analyzed for changes to changes in skin tone (reduction in b* value and increase in L* value) and facial texture as described hereinbelow ("Imaging Method"). Prior to image collection, the participants washed their face with a mild cleanser and then equilibrated for approximately 20 minutes prior to imaging Images were then collected of the right and left side of the participant's face using a digital camera (e.g., Canon EOS-6D DSLR or similar) equipped with a suitable lens for facial imaging (e.g., 60 mm NIKKOR lens or similar), mounted in a standardized illumination and imaging system fitted with head-positioning. A suitable imaging design is the Canfield VISIA and/or OLE imaging system or a similar imaging system capable of standardized and reproducible imaging. The Canfield VISIA and OLE imaging system (Canfield Scientific, Inc., Parsippany, New Jersey, USA) is designed to capture reproducible facial images under controlled lighting and head positioning configurations in clinical research studies. The VISIA and OLE imaging system both incorporate a Canon EOS-6D DSLR which uses a 21-megapixel CMOS sensor with a maximum 5472×3648 resolution. The VISIA and OLE imaging system saves both an Exif JPEG and Canon raw image file for each captured image.

Images of the test subjects are collected under different lighting modalities to enhance visualization of the skin features under investigation. An automated flash selection control and changeable filter control selects for the correct combination of lighting, lighting angles and filters that are optimized for the enhanced imaging of the facial topographical features (wrinkles, texture, etc.) or facial color feature (spots, tone, etc.). Reproducibility from time point to time point is facilitated with the aid of a live feed image of the subject superimposed on the baseline image. The subject is positioned such that all key landmarks on the face of the live image are exactly registered with those same landmarks of the baseline image. Each image contains a color chart with color chips of known values to assist in color management. Images captured with the VISIA and OLE imaging system using the Canfield Capture software are saved directly to the data drive on the imaging system's computer.

In this Example, the region of interest (ROI) for tone and texture measurements covered the test subject's upper and lower cheek, but did not extend into the undereye and central crow's feet areas. The upper limit of the mask followed along the subject's upper cheek bone. Specific differences in ROIs are due to variation in subject facial morphology. The yellowness (b*) and brightness (L*) was analyzed from the cross polarized images which highlights basal skin tone via image analysis and measured as the average b* value and L* value respectively of the ROI. The change in yellowness (Δb*) and brightness (ΔL*) was calculated as the change from baseline at the timepoint of interest (in this case, 8 weeks). For cross study comparisons, the results are adjusted vs. the vehicle control to account for any study differences and are reported as a change from control (treatment effect minus control effect).

The results in table 3 and table 4 are the Δb* change and ΔL* change from vehicle control and associated p-values comparing the test leg and vehicle control respectively. Statistical analysis was conducted using a mixed model with subject (fitted as a random effect), baseline, treatment and side (fitted as fixed effects) as covariates at each time point. The level of significance was 0.10 (2-sided) for study comparisons such that a p-value less than 0.10 was statistically significant. The expected value is calculated by adding the Δb* values of test legs A and B. Synergy factor is calculated by dividing the observed value (test leg C) by the expected value. A synergy factor of greater than 1 indicates a synergistic effect.

As can be seen in Table 3, test leg A had a small but significant b* reduction. Test leg B had an increased significant decrease in b* value. Surprisingly, the inventive composition of test leg C decreased b* value far more than expected, as evidenced by a synergy factor of 3.03. Suitable decreases in b* value herein are −0.200 or more (e.g., −0.300, −0.400, −0.500, or even −1.0 or more).

TABLE 3

Δb* (change vs. vehicle control)

| Test leg | Δb* | P-value |
|---|---|---|
| A (0.9% HCA) | −0.113 | 0.0892 |
| B low-pH, 2% N | −0.226 | 0.0025 |
| C low-pH, 2% N, 1% HCA | −1.028 | <0.0001 |
| Expected (A + B) | −0.339 | — |
| Synergy factor | 3.03 | — |

For skin brightening (L* value), test leg A did not show any skin brightening benefits at 8 weeks while test leg B showed very strong brightening efficacy. Surprisingly, the inventive composition of test leg C increased L* value far more than expected, as evidenced by a synergy factor of 2.35. Suitable increases in L* value herein are greater than 0.2 or more (e.g., 0.2, 0.4, 0.6, or even 1.0 or more).

TABLE 4

ΔL* (change vs. vehicle control)

| Test leg | ΔL* | P-value |
|---|---|---|
| A (0.9% HCA) | −0.072 | 0.3011 |
| B low-pH, 2% N | 0.684 | 0.0002 |
| C low-pH, 2% N, 1% HCA | 1.436 | 0.0001 |
| Expected (A + B) | 0.612 | — |
| Synergy factor | 2.35 | — |

The appearance of skin texture was also evaluated in the studies. The method for determining Texture Area Fraction uses the standardized and reproducible image capture as previously outlined and objective image analysis methodology. The degree of textured skin in the ROI were quantified objectively using image analysis algorithms based on an Optimus software platform. This analysis identified surface skin texture patterns that correlate to human perception of texture and quantified the total texture area detected in terms of pixels. Because the ROI varies in shape and size from subject to subject, the total texture area was normalized to the total ROI size to yield a Texture Area Fraction (TAF), i.e., the fractional ROI area occupied by facial texture in terms of pixels. A summary of the results is provided in Table 5.

As can be seen in Table 5, the inventive composition synergistically improved Texture Area Fraction compared to the comparative test legs values. Comparative test leg A did not improve the appearance of skin texture while test leg B provided a significant improvement in skin texture appearance. Surprisingly, test leg C provided a synergistic improvement in the appearance of skin texture. Suitable decreases in Texture value herein are −0.200 or more (e.g., −0.300, −0.400, −0.500, or even −1.0 or more).

TABLE 5

Texture Area Fraction (change vs. vehicle control)

| Test leg | Texture Area Fraction | P-value |
|---|---|---|
| A (0.9% HCA) | −0.039 | 0.2291 |
| B low-pH, 2% N | −0.215 | 0.0075 |
| C low-pH, 2% N, 1% HCA | −0.341 | 0.0003 |
| Expected (A + B) | −0.254 | — |
| Synergy factor | 1.34 | — |

Example 3: Effect of pH and Niacinamide on HCA Stability

This example demonstrates the effect of pH and niacinamide on HCA stability. When HCA degrades (e.g., via decarboxylation), it produces 4-vinylphenol (4-VP) as a byproduct, which is generally undesirable in a skin care composition. 4-VP can cause the composition to have an unpleasant odor and may further react to cause discoloration (e.g., yellowing) of the composition. Thus, it may be desirable to limit the amount of 4-VP in a skin care composition to less than 1500 ppm (e.g., less than 1100, 800 ppm, 700 ppm, 600 ppm, 500 ppm, 400 ppm, or even less than 300 ppm).

The compositions in Table 6 were tested to determine the effect of pH and niacinamide on the degradation of HCA and the formation of 4-VP. The pH of the test compositions was adjusted using a 6N HCL solution or 4% NaOH solution, as necessary. The test compositions were incubated at 50° C. for 3 weeks, and then tested according to the HPLC method described above for HCA degradation and the color method described above for changes in color (Δb*).

TABLE 6

| Component | 6A | 6B | 6C | 6D | 6E | 6F |
|---|---|---|---|---|---|---|
| | % | | | | | |
| Water | qs | qs | qs | qs | qs | qs |
| HCA | 1.0 | 1.0 | 1.0 | 1.0 | 1.0 | 1.0 |
| Niacinamide | 5 | 5 | 5 | 0 | 0 | 0 |
| Pentylene Glycol | 40 | 40 | 40 | 40 | 40 | 40 |
| pH | 3.56 | 4.57 | 6.17 | 3.45 | 4.52 | 6.10 |
| Results (3W50C) | | | | | | |
| HCA wt % (remaining) | 0.921 | 0.915 | 0.888 | 0.977 | 0.966 | 0.949 |
| 4-Vinylphenol | 380 | 700 | 1070 | 90 | 200 | 490 |
| Color Db* | 3.51 | 0.95 | 6.04 | 0.43 | 0.45 | 1.6 |

As can be seen in Table 6, both pH and niacinamide appear to affect HCA degradation, Δb* and 4-VP formation. These data suggest that increasing pH and/or adding niacinamide will increase the degradation of 4-HCA, increase the formation of 4-VP, and cause yellowing in an aqueous skin care composition. The data unexpectedly show that adding niacinamide actually accelerates the formation of 4-VP at higher pH. This is unexpected because it was previously unknown that niacinamide contributed to HCA degradation at all, let alone accelerated it. Thus, lowering the pH in a skin care composition comprising HCA and niacinamide appears to reduce the rate of formation of 4-VP more than expected.

The data in Table 6 also demonstrate that both pH and niacinamide contribute to the change in yellowness (Δb*) of the test compositions. Surprisingly, a pH of between 3.8 and 6.0 (e.g., about 4.5) appears to provide the lowest Δb* for the test compositions containing niacinamide. This result is surprising because it was believed that yellowing (i.e., a positive change in Δb* value) associated with HCA degradation would change with pH in a predictable linear fashion, as seen in with compositions 6D-6F.

Example 4: Effect of a Radical Scavenger on Rate of Yellowing

This example demonstrates the ability of an antioxidant to help reduce HCA degradation as evidenced by a reduced rate of yellowing (i.e., lower Δb* value). The test compositions shown in Table 7 below were tested with and without sodium metabisulfite, an oxygen-quenching, reducing agent, at pH 3.8 and pH 6.0. The test compositions were aged at two different accelerated aging conditions: 3 weeks at 50° C. (3W50C) and 3 months at 40° C. (3M40C). It is believed, without being limited by theory, that the accelerated aging conditions simulate environmental conditions that a skin care product may be exposed to during shipping and storage. Following the accelerated aging, the test compositions were tested according to the Color method described above to determine Δb*. The test composition aged for 3 months at 40° C. were further tested according to the HPLC method to determine the level of HCA degradation and 4-VP formation.

The results of the testing are summarized in Table 7 below. As can be seen in Table 7, the addition of sodium metabisulfate (SMBS) significantly reduced the rate of yellowing for compositions 7B and 7D, as compared to 7A and 7C, respectively. Surprisingly, the data indicate that the effect of the oxygen quenching reducing agent was enhanced more than expected at low pH vs. neutral pH (i.e., 20% for 3W50C and 240% for 3M40C, as can be seen in Table 7). The reduction in Δb* does not appear to be due to a further reduction of HCA degradation or 4-VP formation, but some other unique mechanism of action. Thus, it is now possible to provide combinations of ingredients that can synergistically reduce the rate of yellowing in a low-pH composition containing HCA

TABLE 7

| Component | 7A | 7B % | 7C | 7D |
|---|---|---|---|---|
| Water | qs | qs | qs | qs |
| Glycerin | 4.5 | 4.5 | 4.5 | 4.5 |
| Dimethicone 5 cSt | 4.00 | 4.00 | 4.00 | 4.00 |
| Niacinamide | 2.00 | 2.00 | 2.00 | 2.00 |
| Lactic acid | 2.00 | 2.00 | — | — |
| Sodium lactate | 0.90 | 0.90 | — | — |
| Polyacrylate crosspolymer-6 | 1.50 | 1.50 | 1.50 | 1.50 |
| Panthenol | 0.50 | 0.50 | 0.50 | 0.50 |
| PEG-11 methyl ether dimethicone | 0.10 | 0.10 | 0.10 | 0.10 |
| Sodium Benzoate | 0.05 | 0.05 | 0.05 | 0.05 |
| 4-HCA | 1.00 | 1.00 | 1.00 | 1.00 |
| PEG-4 | 5.67 | 5.67 | 5.67 | 5.67 |
| Ethoxydiglycol | 20.0 | 20.0 | 20.0 | 20.0 |
| Sodium Metabisulfite | — | 0.05 | — | 0.05 |
| NaOH (adjust to target pH) | — | — | 0.22 | 0.22 |
| pH | 3.8 | 3.8 | 6 | 6 |

TABLE 7-continued

| Component | 7A | 7B % | 7C | 7D |
|---|---|---|---|---|
| Results (3W50C) | | | | |
| Db* value | 7.73 | 2.13 | 10.73 | 6.04 |
| Results (3M40C) | | | | |
| Db* value | 8.42 | 2.11 | 11.35 | 8.71 |
| HCA wt % remaining | 0.891 | 0.891 | 0.907 | 0.882 |
| 4-VP | 623 | 638 | 1044 | 980 |

The synergistic results from the testing in this example are illustrated in Table 8. Synergy factor is calculated by dividing the observed value by the expected value. A synergy factor of greater than 1 indicates a synergistic effect.

TABLE 8

| Synergistic effect of radical scavenger | | |
|---|---|---|
| | 3W50C Db* | 3M40C Db* |
| Control [7C] | 10.73 | 11.35 |
| pH Effect, pH 3.8 vs. pH 6 [7A − 7C] | −3.00 | −2.93 |
| SMBS Effect at pH 6, [7D − 7C] | −4.69 | −2.64 |
| 7B Expected [7D + (7A − 7C)] AND/OR [7B + (7D − 7C)] | 3.04 | 5.78 |
| Expected combined effect [7B$_{expected}$ − 7C] | −7.69 | −5.57 |
| 7B Actual | 2.13 | 2.11 |
| Actual combined effect [7B$_{actual}$ − 7C] | −8.6 | −9.24 |
| Synergy Factor, [7B$_{actual}$ − 7C]/[7B$_{expected}$ − 7C] | 1.12 | 1.66 |

Example 5: Low pH Solubility

Figure 2:
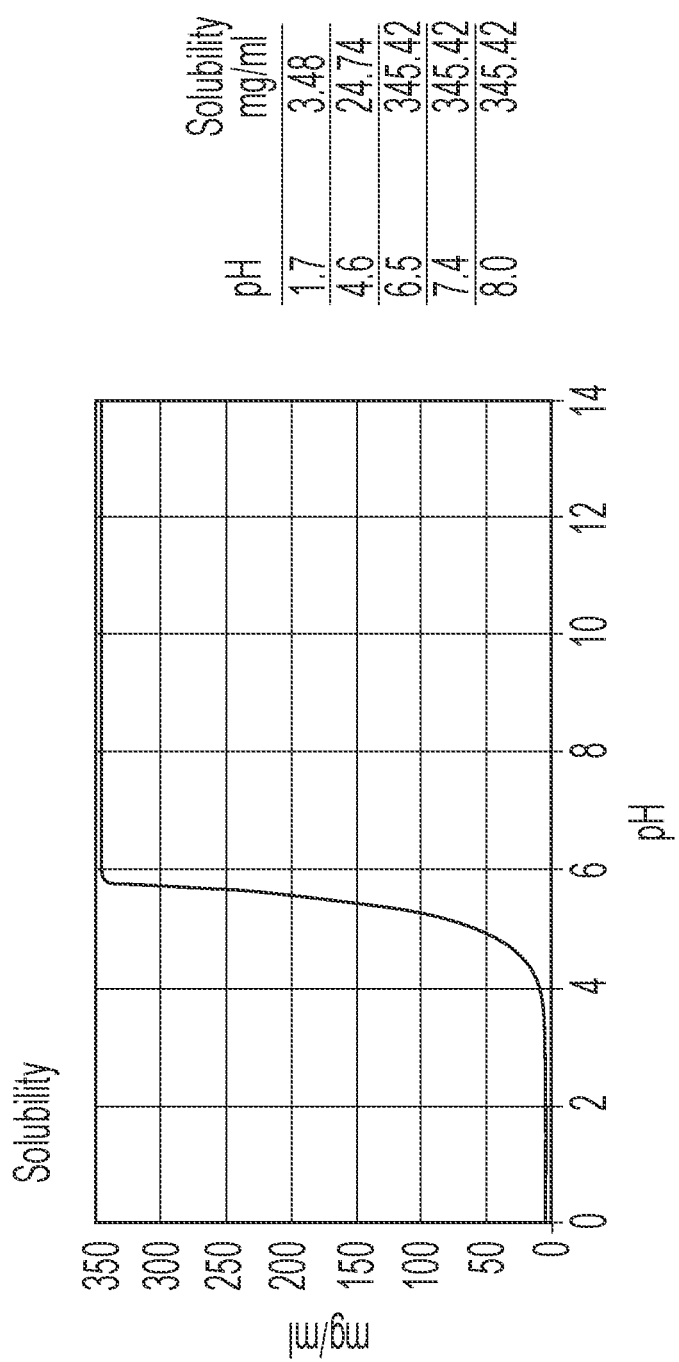
FIG. 2 illustrates HCA solubility in water across a range of pH. Chemicalize was used for prediction of HCA solubility (CAS #501-98-4, 7400-08-0), November 2021, https://chemicalize.com/, developed by ChemAxon.

This example demonstrates the ability of the low-pH compositions herein to solubilize HCA at low pH. As illustrated in FIG. 2, HCA solubility begins to decrease dramatically at approximately pH 6.0. However, the low-pH compositions are able to keep HCA solubilized at low pH (e.g., pH 3.8) as a result of high levels of glycol co-solvents (ethoxydiglycol and PEG-4). The test compositions shown in Table 9 were subjected to 2 freeze/thaw cycles at −7C/25C for 1 week/1 week, totaling one month of temperature cycling, to accelerate potential HCA instability. As can be seen in Table 9, certain test compositions passed the HCA Crystallization test, until the glycol co-solvents levels are reduced to such a level that the HCA is no longer solubilized.

TABLE 9

| Material | 9A | 9B Wt % | 9C |
|---|---|---|---|
| Water | QS | QS | QS |
| Glycerin | 4.5 | 4.5 | 4.5 |
| Dimethicone, 5 cst | 4 | 4 | 4 |
| Niacinamide | 2 | 2 | 2 |
| Ethoxydigycol | 19 | 17 | 15 |
| PEG-4 | 2.83 | 2.83 | 2.83 |
| 4-HCA | 0.5 | 0.5 | 0.5 |
| Lactic acid | 1.8 | 1.8 | 1.8 |
| Sodium lactate | 1.3 | 1.3 | 1.3 |
| Polyacrylate crosspolymer-6 | 1.2 | 1.2 | 1.2 |
| PEG-11 methyl ether dimethicone | 0.1 | 0.1 | 0.1 |
| Total | 100 | 100 | 100 |
| Target pH | 3.8 | 3.8 | 3.8 |
| Freeze/Thaw Crystallization | Pass | Pass | Fail |

Example 6: Effect of Glycol Co-Solvent and Phenolic Acid Salt Hydrotrope on HCA Solubility The example demonstrates how a glycol can improve the solubility of HCA. While it is desirable to formulate HCA containing compositions at lower pH to reduce 4-VP production and yellowing, the solubility of the HCA at low pH may not be sufficient for it to be added at levels needed for an effective skin care active. Similar to Example 5, the test compositions shown in Table 10 were subjected to 2 freeze/thaw cycles at −7C/25C for 1 week/1 week, totaling one month of temperature cycling. In this example, the phenolic acid is neutralized with an aqueous basic solution (e.g., sodium hydroxide) to form the ionized salt form of the species in-situ during batch making. The results of the testing are summarized in Table 10 below.

As can be seen in Table 10, inventive combinations containing a suitable combination of hydrotrope and glycol co-solvent are free of HCA crystals ("pass"), while comparative examples demonstrate crystal formation ("fail"). The combination of ethoxydiglycol and sodium salicylate was able to solubilize 0.5% HCA in the low-pH aqueous composition, even when the level of glycol cosolvent is not sufficient alone. Further, as can be seen from the data, the addition of sodium salicylate reduces the amount of glycol to solubilize the HCA and, more importantly, remain below a level that might result in undesirable feel problem (e.g., <25% combined glycol cosolvents). Other well-known hydrotropes such as caffeine and niacinamide are unable to solubilize the HCA, even at higher levels (5%). Testing additional phenolic acids and phenolic alcohols should reveal that phenolic acids with a pKA less than the pH formulated, in this case 3.8, are more effective at solubilizing HCA than other traditional hydrotropes or chemicals of similar structural characteristics.

TABLE 10

| Material | 10A | 10B | 10C Wt % | 10D | 10E |
|---|---|---|---|---|---|
| Water | QS | QS | QS | QS | QS |
| Glycerin | 4.5 | 4.5 | 4.5 | 4.5 | 4.5 |
| Dimethicone, 5 cst | 4 | 4 | 4 | 4 | 4 |
| Niacinamide | 2 | 2 | 2 | 2 | 2 |
| Ethoxydigycol | 15 | 15 | 15 | 15 | 15 |
| 4-HCA | 0.5 | 0.5 | 0.5 | 0.5 | 0.5 |
| PEG-4 | 2.83 | 2.83 | 2.83 | 2.83 | 2.83 |
| Lactic acid | 1.8 | 1.8 | 1.8 | 1.8 | 1.8 |
| Sodium lactate | 1.3 | 1.3 | 1.3 | 1.3 | 1.3 |
| Polyacrylate crosspolymer-6 | 1.2 | 1.2 | 1.2 | 1.2 | 1.2 |
| PEG-11 methyl ether dimethicone | 0.1 | 0.1 | 0.1 | 0.1 | 0.1 |
| Caffeine | — | — | 5 | — | — |
| Sodium Cinnamate | — | — | — | 1.5 | — |
| Sodium Salicylate | 1.5 | — | — | — | — |
| 2,4-Dihydroxybenzoic Acid | — | — | — | — | 1.5 |
| 3,4-Dihydroxybenzoic Acid | — | — | — | — | — |
| 2,3-Dihydroxybenzoic acid | — | — | — | — | — |
| 3-Methoxysalicylic Acid | — | — | — | — | — |
| Sodium hydroxide (pH adjuster) | * | * | * | * | * |
| Total | 100 | 100 | 100 | 100 | 100 |
| Target pH | 3.8 | 3.8 | 3.8 | 3.8 | 3.8 |
| Freeze/Thaw Crystallization | Pass | Fail | Fail | Fail | Pass |

| Material | 10F | 10G Wt % | 10H |
|---|---|---|---|
| Water | QS | QS | QS |
| Glycerin | 4.5 | 4.5 | 4.5 |
| Dimethicone, 5 cst | 4 | 4 | 4 |
| Niacinamide | 2 | 2 | 2 |
| Ethoxydigycol | 15 | 15 | 15 |
| 4-HCA | 0.5 | 0.5 | 0.5 |
| Lactic acid | 1.8 | 1.8 | 1.8 |
| Sodium lactate | 1.3 | 1.3 | 1.3 |
| Polyacrylate crosspolymer-6 | 1.2 | 1.2 | 1.2 |
| PEG-11 methyl ether dimethicone | 0.1 | 0.1 | 0.1 |
| Caffeine | — | — | — |
| Sodium Cinnamate | — | — | — |
| Sodium Salicylate | — | — | — |
| 2,4-Dihydroxybenzoic Acid | — | — | — |
| 3,4-Dihydroxybenzoic Acid | 1.5 | — | — |
| 2,3-Dihydroxybenzoic acid | — | 1.5 | — |
| 3-Methoxysalicylic acid | — | — | 1.5 |
| Sodium hydroxide (pH adjuster) | * | * | * |
| Total | 100 | 100 | 100 |
| Target pH | 3.8 | 3.8 | 3.8 |
| Freeze/Thaw Crystallization | Fail | Pass | Pass |

*Sodium Hydroxide used as a pH adjuster as needed to target pH levels and neutralize phenolic acids

Example 7: Solubility Effect of Mixing HCAs

This example demonstrates the unexpected improvement in solubility of a 50:50 mixture of coumaric acid and ferulic acid, even in the absence of a hydrotrope. The test compositions shown in Table 11 were subjected to 2 freeze/thaw cycles at −7C/25C for 1 week/1 week, totaling one month of temperature cycling. As can be seen in Table 11, test composition 11B did not exhibit significant HCA crystallization even in the absence of an additional hydrotrope or polar emollient, and the combination of ferulic acid and coumaric acid in composition 11B appears to provide a synergistic boost in HCA solubility.

TABLE 11

| Material | 11A | 11B |
|---|---|---|
| | Wt % | |
| Water | QS | QS |
| Glycerin | 4.5 | 4.5 |
| Dimethicone, 5 cst | 4 | 4 |
| Niacinamide | 2 | 2 |
| Ethoxydigycol | 15 | 15 |
| 4-HCA | 0.50 | 0.25 |
| Ferulic Acid | — | 0.25 |
| Lactic acid | 1.8 | 1.8 |
| Sodium lactate | 1.3 | 1.3 |
| Polyacrylate crosspolymer-6 | 1.2 | 1.2 |
| PEG-11 methyl ether dimethicone | 0.1 | 0.1 |
| Total | 100 | 100 |
| Target pH | 3.8 | 3.8 |
| Freeze/Thaw Crystallization | Fail | Pass |

Example 8: Comparative Examples

This example demonstrates the inability of conventional compositions to solubilize HCA at low pH. Example 2 of U.S. Publication number 2014/0107046 was prepared as described in the application, along with several variations of that formula (Examples A to K). The test compositions are shown below in Table 12. The test compositions were subjected to 2 freeze/thaw cycles at −7C/25C and 1 week/1 week, followed by a 90-day rest period at 25° C. The compositions were then examined for the presence of HCA crystals, as described above. As can be seen in Table 12, all of the comparative compositions exhibited crystallization/precipitation. Even when p-coumaric acid is substituted for ferulic acid, as in comparative compositions C, I and J, the comparative compositions still exhibited HCA crystallization. Thus, none of the comparative compositions exhibit the desired HCA solubility provided by the low-pH compositions herein.

TABLE 12

| Phase | Material | 12A | 12B | 12C | 12D | 12E | 12F | 12G |
|---|---|---|---|---|---|---|---|---|
| A | Propylene glycol | 10 | 10 | 10 | 10 | 10 | 10 | 10 |
| A | Dipropylene glycol | 10 | 10 | 10 | 10 | 10 | 10 | 10 |
| A | Ethanol | 10 | 10 | 10 | 10 | 10 | 10 | 10 |
| A | Ferulic acid | 0.5 | 0.5 | — | 0.5 | 0.5 | 0.5 | 0.5 |
| A | p-Coumaric acid | — | — | 0.5 | — | — | — | — |
| A | Baicalin | 0.4 | — | — | — | — | — | — |
| B | Water | 49 | 49.5 | 49.5 | 49.5 | 49.5 | 49.5 | 54.5 |
| B | Vitamin C | 10 | 10 | 10 | 10 | 10 | 10 | 10 |
| B | Caffeine | 5 | 5 | 5 | 5 | 5 | 5 | — |
| B | Nicotinamide | 5 | 5 | 5 | 5 | 5 | 5 | 5 |
| B | Baicalin | 0.1 | — | — | — | — | — | — |
| C | 10% NaOH | * | * | * | * | * | * | * |
| C | HCl | * | * | * | * | * | * | * |
| | Total | 100 | 100 | 100 | 100 | 100 | 100 | 100 |
| | Target pH | 4.5 | 4.5 | 4.5 | 4 | 3.5 | 3 | 3.8 |
| | Freeze/Thaw Crystallization? | Fail | Fail | Fail | Fail | Fail | Fail | Fail |

| Phase | Material | 12H | 12I | 12J | 12K |
|---|---|---|---|---|---|
| A | Propylene glycol | 10 | 10 | 10 | 10 |
| A | Dipropylene glycol | 10 | 10 | 10 | 10 |
| A | Ethanol | 10 | 10 | 10 | — |
| A | Ferulic acid | 0.5 | — | — | 0.5 |
| A | p-Coumaric acid | — | 0.5 | 0.5 | — |
| A | Baicalin | — | — | — | — |
| B | Water | 59.5 | 54.5 | 59.5 | 69.5 |
| B | Vitamin C | 10 | 10 | 10 | 10 |
| B | Caffeine | — | — | — | — |
| B | Nicotinamide | — | 5 | — | — |
| B | Baicalin | — | — | — | — |
| C | 10% NaOH (pH adjuster) | * | * | * | * |
| C | HCl (pH adjuster) | * | * | * | * |
| | Total | 100 | 100 | 100 | 100 |
| | Target pH | 3.8 | 3.8 | 3.8 | 3.8 |
| | Freeze/Thaw Crystallization? | Fail | Fail | Fail | Fail |

Example: Increasing Skin Appearance Stability

An in-vivo imaging study was conducted with the eMR Pro device as detailed in the methods overview section was used to test visual skin appearance stability by measuring day-to-day appearance fluctuations. The study was conducted with a base size of sixty-six test panelists who were healthy japanese women aged between 22 and 35. The panelists self-reported at least 2 of the following skin issues on their cheeks; uneven tone, dark spots, visible pores, oily skin in total for recruitment. Exclusion criteria included: illness, pregnancy, skin disease or allergy, currently under the care of a Dermatologist, history of cosmetic surgery/procedures, experiences red, tight, flaky skin after washing face, has self-reported dry skin, consistently experiences more than 5 large acne lesions (>2 mm, per side of face)

The study was a split-face round robin design across three treatments detailed in table 13. The formulations tested included a placebo leg (composition A), low pH niacinamide (composition B), and low pH niacinamide plus HCA (composition C). The product treatments were randomized for the combinations and side of face. Consumers captured a photo of their left and right cheeks three times a day using eMR Pro (in the morning before face wash after blotting face with tissue paper, in the morning more than 5 min. after face wash, and in the evening more than 5 min. after face wash).

TABLE 13

| Component | 13A | 13B | 13C |
|---|---|---|---|
| Water | qs | qs | qs |
| Glycerin | 4.50 | 4.50 | 4.50 |
| Dimethicone 5 cSt | 4.00 | 4.00 | 4.00 |
| Niacinamide | 2.00 | 2.00 | 2.00 |
| Lactic acid | — | 1.80 | 2.00 |
| Sodium lactate | — | 1.30 | 0.90 |
| Polyacrylate crosspolymer-6 [1] | 1.20 | 1.50 | 1.50 |
| D-Panthenol | 0.50 | 0.50 | 0.50 |
| Disodium EDTA | 0.10 | 0.10 | 0.10 |

TABLE 13-continued

| Component | 13A | 13B | 13C |
|---|---|---|---|
| PEG-11 methyl ether dimethicone [3] | 0.10 | 0.10 | 0.10 |
| Trehalose | 0.10 | 0.10 | 0.10 |
| Sodium benzoate | 0.05 | 0.05 | 0.05 |
| 4-HCA [4] | — | — | 1.00 |
| PEG-4 | — | — | 5.67 |
| Ethoxydiglycol | — | — | 20.00 |
| Benzyl Alcohol | 0.20 | — | — |
| Phenoxyethanol | 0.25 | — | — |
| Methyl Paraben | 0.20 | — | — |
| pH | 4.7 | 3.8 | 3.8 |

The study included a normalization period of 4 weeks where they were given a consistent and basic regimen including a commercially available make-up removal oil, cleansing foam, clear lotion, milky lotion, and UV sunscreen for four weeks. After the normalization period, the consumers added the essence/serum formulations in Table 13 to their regimen. The test products were then used for four additional weeks for the assessment of skin stability by fluctuation measurements.

Statistical analysis was conducted using a mixed model with subject as a random effect while baseline unevenness, treatment, and side as fixed effects as covariates at each time point. The level of significance was 0.10 (2-sided) for all study comparisons such that a p-value less than 0.10 was considered statistically significant. The adjusted means and comparison p-values are reported in table 14, 15, 16. The results for the comparison differences are specified as either versus the vehicle control, normalization period, or between treatment comparison.

TABLE 14

| Test leg | Fluctuation Parameter | Comparison | Timepoint | D Value (Test - Comparison) | P-value |
|---|---|---|---|---|---|
| B, low pH Nia | L* unevenness | Vehicle (A) | Evening | 0.0103 | NS |
| B, low pH Nia | b* unevenness | Vehicle (A) | Evening | −0.0180 | NS |
| C, low pH Nia + HCA | L* unevenness | Vehicle (A) | Evening | −0.0172 | 0.08 |
| C, low pH Nia + HCA | b* unevenness | Vehicle (A) | Evening | −0.0235 | 0.02 |

TABLE 15

| Test leg | Fluctuation Parameter | Comparison | Timepoint | D Value | P-value |
|---|---|---|---|---|---|
| B, low pH Nia | a* mean | Normalization | Evening | 0.01 | NS |
| C, low pH Nia + HCA | a* mean | Normalization | Evening | −0.190 | 0.06 |

TABLE 16

| Test leg | Fluctuation Parameter | Comparison | Timepoint | D Value | P-value |
|---|---|---|---|---|---|
| C, low pH Nia + HCA | L* unevenness | B, low pH Nia | Evening | −0.0275 | 0.04 |
| C, low pH Nia + HCA | Texture unevenness | B, low pH Nia | Evening | −0.0212 | 0.02 |

Examples/Combinations

1. A method of improving the appearance of skin, comprising:
   a) identifying a target portion of skin where treatment is desired;
   b) applying a low-pH, aqueous skin care composition to the target portion of skin over the course of a treatment period, the composition comprising;
      i) about 0.1% to about 10% of a vitamin B3 compound,
      ii) about 0.1% to about 10% of a hydroxycinnamic acid (HCA),
      and
      iii) water, wherein the pH of the composition is less than 5.0.
2. The method of the preceding feature, wherein the improving the appearance of skin is improving sallow looking skin, improving skin texture; and/or improving skin stability.
3. The method of any of the preceding features, wherein the improving the appearance of skin is improving sallow looking skin.
4. The method of any of the preceding features, wherein the method provides at least one of a decrease in b* value, an increase in L* value, or a decrease in skin texture value during the treatment period.
5. The method of any of the preceding features, wherein the decrease in b* value is at least −0.20, the increase in L* value is at least 0.25, and/or the decrease in skin texture value is at least −0.25, according to the Imaging Method.
6. The method of any of the preceding features, wherein the decrease in b* value, increase in L* value, and/or a decrease in skin texture value is synergistic.
7. The method of any of the preceding features, wherein the composition is free of HCA crystals.
8. The method of any of the preceding features, wherein the vitamin B3 compound is niacinamide.
9. The method of any of the preceding features, wherein the composition further comprises a hydrotrope selected from salicylic acid, 2,4 dihydroxybenzoic acid, 2,3 dihydroxybenzoic acid, 3-methoxy salicylic acid, salts of these, and combinations thereof.

10. The method of any of the preceding features, wherein the composition further comprises less than 25% of a glycol co-solvent.
11. The method of any of the preceding features, wherein the co-solvent is selected from the group consisting of propylene glycol, dipropylene glycol, butylene glycol, pentylene glycol, hexylene glycol, ethoxydiglycol, C2-C6 polyethene glycols, and combinations thereof.
12. The method of any of the preceding features, wherein the composition further comprises about 1% to about 20% by weight of an antioxidant
13. The method of any of the preceding features, wherein the antioxidant is selected from the group consisting of sodium sulfite, sodium bisulfite, sodium metabisifulite, and combinations thereof.
14. The method of any of the preceding features, wherein the pH is about 2.0 to about 4.5.
15. The method of any of the preceding features, wherein the HCA is coumaric acid.
16. The method of any of the preceding features, wherein the composition exhibits less than 25% HCA degradation according to the HPLC method.
17. The method of any of the preceding features, wherein the composition comprises less than 1000 ppm 4-vinylphenol.
18. A method of improving the appearance of skin, comprising:
    a) identifying a target portion of skin where treatment is desired; and
    b) applying a low-pH, aqueous skin care composition to the target portion of skin over the course of a treatment period, the composition comprising
        i) a vitamin B3 compound,
        ii) a mixture of coumaric acid and ferulic acid, wherein the ratio of coumaric acid to ferulic acid is about 2:1 to about 1:2, and
        iii) water, wherein the composition has a pH of about 5.0 or less.
19. The method of the preceding feature 18, wherein the weight ratio of coumaric acid to fumaric acid is about 1:1.
20. The method of the preceding feature 18, wherein the method provides in a synergistic improvement in at least one of b* value, L* value, and skin texture value during the treatment period.
21. The method of the preceding feature 18, wherein the composition further comprises a hydrotrope selected from salicylic acid, 2,4 dihydroxybenzoic acid, 2,3 dihydroxybenzoic acid, 3-methoxy salicylic acid, salts of these, and combinations thereof.
22. The method of the preceding feature 18, wherein the composition is free of HCA crystals.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of improving the appearance of skin, comprising:
    a) identifying a target portion of skin where treatment is desired;
    b) applying a low-pH, aqueous skin care composition to the target portion of skin over the course of a treatment period, the composition comprising:
        i) about 0.1% to about 10% of a vitamin B3 compound,
        ii) about 0.1% to about 10% of a coumaric acid,
        iii) a glycol co-solvent chosen from propylene glycol, dipropylene glycol, butylene glycol, pentylene glycol, hexylene glycol, ethoxydiglycol, C2-C6 polyethene glycols, or mixtures thereof; wherein the composition comprises less than 25% of the glycol co-solvent;
        iv) one or more hydrotrope chosen from salicylic acid, 2,4 dihydroxybenzoic acid, 2,3 dihydroxybenzoic acid, 3-methoxy salicylic acid, salts of these, or mixtures thereof; and
        v) water,
    wherein the composition is free of coumaric acid crystals; wherein the pH of the composition is less than 5.0.

2. The method of claim 1, wherein the improving the appearance of skin is improving sallow looking skin, improving skin texture, and/or improving skin stability.

3. The method of claim 1, wherein the method provides at least one of a decrease in b* value or an increase in L*value during the treatment period, wherein the b* value and/or the L* value are determined according to the Imaging Method.

4. The method of claim 3, wherein the decrease in b* value is at least −0.20 and/or the increase in L* value is at least 0.25, wherein the b* value and the L* value are determined according to the Imaging Method.

5. The method of claim 3, wherein the decrease in b* value and/or the increase in L* value has a synergy factor of greater than 1.

6. The method of claim 1, wherein the vitamin B3 compound is niacinamide.

7. The method of claim 1, wherein the one or more hydrotrope comprising salicylic acid.

8. The method of claim 7, wherein the co-solvent comprises ethoxydiglycol.

9. The method of claim 1, wherein the composition comprises less than 17% of the glycol co-solvent.

10. The method of claim 1, wherein the composition further comprises about 1% to about 20% by weight of an antioxidant.

11. The method of claim 10, wherein the antioxidant is selected from the group consisting of sodium sulfite, sodium bisulfite, sodium metabisifulite, and combinations thereof.

12. The method of claim 1, wherein the pH of the composition is about 2.0 to about 4.5.

13. The method of claim 1, wherein the composition exhibits less than 25% coumaric acid degradation, according to the HPLC method.

14. The method of claim 1, wherein the composition comprises less than 1000 ppm 4-vinylphenol.

15. The method of claim 1, wherein the composition further comprises a buffering system comprising lactic acid and sodium lactate.

16. A method of improving the appearance of skin, comprising:
   a) identifying a target portion of skin where treatment is desired; and
   b) applying a low-pH, aqueous skin care composition to the target portion of skin over the course of a treatment period, the composition comprising:
      i) a vitamin B3 compound,
      ii) a hydroxycinnamic acid (HCA) comprising a mixture of coumaric acid and ferulic acid, wherein the ratio of coumaric acid to ferulic acid is about 2:1 to about 1:2, and
      iii) water, wherein the composition has a pH of about 5.0 or less;
      wherein the composition is free of HCA crystals.

17. The method of claim 16, wherein the weight ratio of coumaric acid to ferulic acid is about 1:1.

18. The method of claim 16, wherein the decrease in a b* value and/or the increase in a L* value during the treatment period has a synergy factor of greater than 1; wherein the b* value and the L* value are determined according to the Imaging Method.

19. The method of claim 16, wherein the composition further comprises ethoxydiglycol and salicylic acid, salts of these, or a combination thereof.

* * * * *